(12) United States Patent
Herrmann

(10) Patent No.: US 11,087,921 B2
(45) Date of Patent: Aug. 10, 2021

(54) INDUCTIVE ROTARY JOINT WITH U-SHAPED FERRITE CORES

(71) Applicant: SCHLEIFRING GMBH, Furstenfeldbruck (DE)

(72) Inventor: Ulrich Herrmann, Munich (DE)

(73) Assignee: SCHLEIFRING GMBH

( * ) Notice: Subject to any disclaimer, the term of this patent is extended or adjusted under 35 U.S.C. 154(b) by 1054 days.

(21) Appl. No.: 14/958,573

(22) Filed: Dec. 3, 2015

(65) Prior Publication Data

US 2016/0181013 A1   Jun. 23, 2016

(30) Foreign Application Priority Data

Dec. 18, 2014   (EP) .................................... 14198919

(51) Int. Cl.

| | | |
|---|---|---|
| H01F 21/06 | (2006.01) | |
| H01F 21/04 | (2006.01) | |
| H01F 38/18 | (2006.01) | |
| A61B 6/00 | (2006.01) | |
| H02J 50/10 | (2016.01) | |
| H01F 27/36 | (2006.01) | |
| H02J 5/00 | (2016.01) | |
| H01F 27/255 | (2006.01) | |
| H01F 27/26 | (2006.01) | |

(Continued)

(52) U.S. Cl.
CPC ............. *H01F 38/18* (2013.01); *A61B 6/56* (2013.01); *H01F 27/255* (2013.01); *H01F 27/263* (2013.01); *H01F 27/2823* (2013.01); *H01F 27/36* (2013.01); *H02J 5/005* (2013.01); *H02J 50/10* (2016.02); *A61B 6/032* (2013.01); *H01F 27/266* (2013.01)

(58) Field of Classification Search
USPC ... 336/120, 116–119, 192, 178, 83, 130–136
See application file for complete search history.

(56) References Cited

U.S. PATENT DOCUMENTS

| | | | |
|---|---|---|---|
| 5,572,175 A | 11/1996 | Tada et al. | |
| 5,572,178 A * | 11/1996 | Becker | H01F 38/18 336/120 |
| 5,715,591 A | 2/1998 | Albrecht et al. | |

(Continued)

FOREIGN PATENT DOCUMENTS

| | | |
|---|---|---|
| CN | 101026033 A | 8/2007 |
| CN | 201397738 Y | 2/2010 |

(Continued)

OTHER PUBLICATIONS

Office Action issued in related Chinese Patent Application No. 201511035793.1, dated Feb. 23, 2019, 7 pages.

*Primary Examiner* — Shawki S Ismail
*Assistant Examiner* — Kazi S Hossain
(74) *Attorney, Agent, or Firm* — Yakov Sidorin; Quarles & Brady LLP

(57) ABSTRACT

A rotating power transformer comprises a primary magnetic core with a primary winding and a secondary magnetic core with a secondary winding. The magnetic cores preferably comprise a ferrite material and are U-shaped, and have a base connecting two legs. The width of the legs is significantly larger than the height of the base, resulting in a better magnetic coupling and a significantly improved tolerance to mechanical deviations.

17 Claims, 4 Drawing Sheets

(51) Int. Cl.
    *H01F 27/28*     (2006.01)
    *A61B 6/03*     (2006.01)

(56) References Cited

U.S. PATENT DOCUMENTS

| | | | |
|---|---|---|---|
| 6,982,623 B2 * | 1/2006 | Satou | H01F 3/10 |
| | | | 336/178 |
| 2003/0173936 A1 | 9/2003 | Sezgin et al. | |
| 2006/0022785 A1 * | 2/2006 | Dobbs | A61B 6/56 |
| | | | 336/120 |
| 2012/0082288 A1 | 4/2012 | Friesner et al. | |
| 2012/0293291 A1 * | 11/2012 | Cheng | H01F 27/292 |
| | | | 336/65 |
| 2013/0187740 A1 | 7/2013 | Loiselle et al. | |
| 2013/0214614 A1 * | 8/2013 | Krumme | A61B 6/56 |
| | | | 307/104 |
| 2015/0022306 A1 * | 1/2015 | Scholz | H01F 27/2804 |
| | | | 336/200 |
| 2015/0061817 A1 * | 3/2015 | Lee | H01F 17/0013 |
| | | | 336/221 |

FOREIGN PATENT DOCUMENTS

| | | |
|---|---|---|
| CN | 102551775 A | 7/2012 |
| CN | 103260517 A | 8/2013 |
| DE | 10 2010 041836 | 4/2012 |
| JP | 2000058355 A | 9/2001 |
| JP | 2001250795 A | 9/2001 |
| WO | 2008094919 A2 | 8/2008 |
| WO | 2011146065 A1 | 11/2011 |
| WO | 2012003999 A2 | 1/2012 |
| WO | 2012041554 A1 | 4/2012 |

\* cited by examiner

INDUCTIVE ROTARY JOINT WITH U-SHAPED FERRITE CORES

CROSS-REFERENCE TO RELATED APPLICATIONS

This application claims priority from and benefit of European Application No. 14198919.4 filed on Dec. 18, 2014, the disclosure of which is incorporated herein by reference.

BACKGROUND

Field of the Invention

The invention relates to contactless rotary joints and, specifically, to contactless rotary joints configured to transfer high levels of electrical power, also called rotating power transformers. Such contact-less rotary joints may be used in CT scanners.

Description of Relevant Art

A contactless rotary joint comprising an inductive power coupler is disclosed in U.S. Pat. No. 7,197,113 B1. Such a rotary joint is able to transfer power of more than hundred kilowatts from a stationary part to a rotating part. Such rotary joints have heavy iron or ferrite cores for guiding the magnetic fields. For example, in CT scanners a free bore diameter of more than one meter is required. Accordingly, the inner diameter of such a rotary joint may be more than 1 meter requiring large and massive mechanical support structures.

The European patent publication EP 1 481 407 B1 discloses a rotating transformer with a winding form made of a plurality of shaped parts held within a U-shaped ring.

An inductive rotary joint having U-shaped ferrite cores is further disclosed in U.S. Pat. No. 5,608,771.

SUMMARY

The embodiments are directed to improving rotating power transformers by simplifying the mechanical design, and increasing robustness and the ability to withstand large centrifugal forces and reliability while decreasing weight.

In an embodiment, a rotating power transformer has a stationary part and a rotating part. Herein the basic structure and function of such parts are shown. Generally it is preferred, when the rotating transformer is symmetrical, having basically identical stationary and rotating parts. Of course, these parts may differ to meet specific needs of the stationary or rotating parts like in the means for fixation to a machine. At least one of the stationary and rotating parts, preferably both are based on a body which preferably is ring shaped. It may have the shape of a disk or a drum. The main function of the body is to give a stable support to the electric and magnetic components of the rotating power transformer. The body may be further supported by parts of a machine, like a CT scanner, into which the power transformer is integrated. The body may be made of metal, like aluminum or of plastic material which preferably is further reinforced. It is preferred, to make the body from electrically isolating and non-magnetic material. The body preferably has circular shape. It may also have different shapes adapted to the machine.

The rotating power transformer further has a primary side and a secondary side. The primary side may either be at the stationary side or at the rotating side, whereas the secondary side is at the other side. The primary side has at least a primary winding comprising at least one primary turn. The secondary side comprises at least one secondary winding having at least one secondary turn. For guiding the magnetic fields between the primary and secondary side, a magnetic material, preferably a soft magnetic material is provided. Most preferably, the magnetic material is a ferrite material. In an alternate embodiment, an iron powder material may be used. Whereas the ferrite material is preferred for higher frequencies, the iron powder material offer a higher Q at lower frequencies. Both materials offer high mechanical strength and can be machined precisely to desired dimensions. Most preferably, ferrite is used due to its high hardness and low thermal expansion. Ferrite materials may be precision machined by grinding, which allows a precise definition of an airgap between the rotating parts.

As in large devices, like in CT scanners, the rotating power transformer has a diameter of about 0.5 m to 1.5 m, it is impossible to build a magnetic core of one piece. Instead, the magnetic cores for coupling the magnetic fields are assembled from a plurality of small segments.

As known in the art, magnetic cores are designed such that the magnetic cross-section is approximately constant along the magnetic path, resulting in a constant flux density through the cores. In case of a non-constant cross-section, the section of a magnetic core having the smallest cross-section will be saturated first under high flux densities. This will lead to a reduced inductance and heat dissipation in the magnetic core. Therefore, it is desirable to have a constant magnetic cross-section to obtain the broadest operating range with minimized ferrite material requirement. Accordingly, standard U-shaped ferrite cores have a pair of legs and a base with the same cross section of ferrite material.

Tests with a large number of magnetic materials and ferrite cores as well as magnetic simulations and calculations have shown that a magnetic core for a rotating power transformer should be designed differently. In contrast to the prior art, the legs have a significantly larger cross-section than the base. Preferably, assuming a constant thickness, the width of each leg is between 1.5- to 5-times the height of the base. Most preferably, the width of each leg is between 2- and 3-times the height of the base. In a most preferred embodiment, the width of each leg is about 2.5-times the base height.

When designing normal magnetic cores like for stationary transformers, an air gap must not be considered, as this is negligible. In rotating power transformers, there is at least a minimum air gap of 0.1 mm which may be up to 3 mm. Tests have shown, that this air gap is not constant. It changes with rotation due to asymmetries in the mounting. Furthermore, due to the large weight of the rotating part in CT scanners, there is a non-negligible effect of gravitational forces further deforming the parts and resulting in an air gap with non-constant size. Tests under large electrical powers have shown that there are also significant magnetic forces when operating the rotating transformer with high magnetic flux, which also leads to a further change of the geometry of the air gap. By using significantly broader legs, the magnetic coupling is improved. The magnetic flux is distributed over a larger area of the larger legs. This results in a better coupling, a larger main inductivity of the transformer, which further results in lower losses in an inverter driving the transformer. Due to the wider legs, the stray flux outside of the area between the legs is also significantly reduced. Therefore, the influence of and to external components is minimized and the losses in the windings of the rotating power transformer are also reduced as the magnetic field penetrating into the windings is reduced. Another benefit of the wide legs is an increased tolerance against displacement between the primary and secondary cores' legs.

In a further embodiment, the magnetic cores are held by a base body which may be a circular drum, cylinder, or disk. Preferably, the base body has a groove for holding the magnetic cores. It is further preferred, if the width of the groove is larger than the width of the magnetic cores, generating a gap between a side wall of the groove and a side wall of the cores. It is further preferred, if this gap is at least partially filled with a filler. This filler may be a soft or elastic material to compensate for forces generated by thermal expansion of the materials of the base and the cores. In a preferred embodiment, where the base is of a plastic material and the magnetic cores are of a ferrite material, both materials have a different thermal expansion coefficient resulting in different expansion when temperature changes. Therefore, the ferrite cores may expand differently than the gap in the base body, such that the gap in the base body may either be too narrow or too wide for the magnetic cores. An elastic filler in the gap may help to hold the magnetic cores in the gap. It is further preferred, with defined thermal expansion coefficients of the magnetic cores, the filler, and the base body, that the dimensions are selected such that the thermal expansion of the magnetic cores plus the thermal expansion of the filler is identical to the thermal expansion of the gap in the base body.

In another embodiment, the ferrite cores have a winding space height and a winding space width which is adapted to the size of the wire wound into the winding space. In a preferred embodiment, a certain number of turns which may be between 2 and 10 turns, is wound into the winding space of the magnetic cores. Preferably, the turns are wound in one layer. This may help to keep parasitic capacitances low and simplify the mechanical assembly. It is now preferred, if the winding space width is approximately N-times the winding space height with a number N of the windings.

According to a further embodiment, a shield is provided around the magnetic cores. The shield may be made of a thin layer of a conductive material, like aluminum or copper. The shield may be provided under the at least one magnetic core or mounted to the side of the body which is opposite to the groove.

In a preferred embodiment, the shield is placed on the backside of the body forming a closed ring with roughly same dimensions as the ferrite but overlapping them (smaller inner and larger outer diameter). The ring may comprise overlapping ring segments, preferably of sheet metal bolted or soldered or welded together. The sheet metal can serve as magnetic shield reducing magnetic stray fields and as electric shield defining capacitive parasitic currents when connected (directly or through a capacitor) to a ground potential or a potential of the power circuitry.

In a further preferred embodiment, the magnetic cores are U-shaped. According to another embodiment, there may also be used E-shaped ferrite cores, where the leg width is also larger than the base height.

BRIEF DESCRIPTION OF THE DRAWINGS

In the following, the invention will be described by way of example, without limitation of the general inventive concept, on examples of embodiment and with reference to the drawings.

Figure 1:
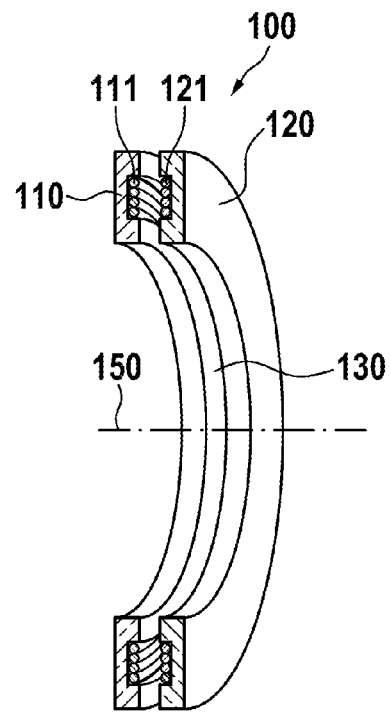
FIG. 1 shows a first embodiment of a disk-shaped rotating power transformer.

While embodiments of the invention can be modified and altered, specific embodiments thereof are shown by way of example in the drawings and further described in detail. It should be understood, however, that the drawings and detailed description are not intended to limit the invention to the particular form disclosed, but on the contrary, the intention is to cover all modifications, equivalents and alternatives falling within the spirit and scope of the present invention as defined by the appended claims.

DETAILED DESCRIPTION

In FIG. 1, a first embodiment of a disk-shaped rotating power transformer 100 is shown. A primary magnetic core 110 having a primary winding 111 is rotatable against a secondary magnetic core 120 having a secondary magnetic winding 121. Between the primary magnetic core 110 and the secondary magnetic core 120 is an air gap 130 in a plane orthogonal to the rotation axis 150.

Figure 2:
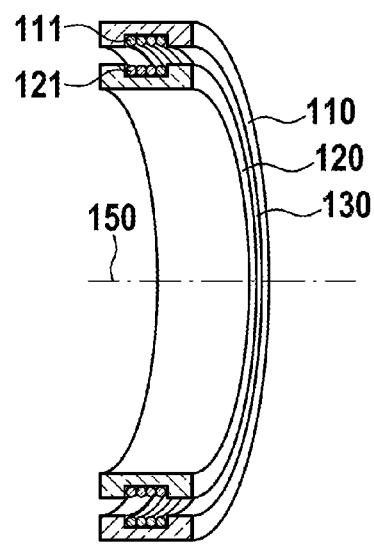
FIG. 2 shows a second embodiment of a drum-shaped rotating power transformer.

In FIG. 2, a second embodiment of a drum-shaped rotating power transformer is shown. A primary magnetic core 110 having a primary winding 111 is rotatable against a secondary magnetic core 120 having a secondary magnetic winding 121. Between the primary magnetic core 110 and the secondary magnetic core 120 is an air gap 130 on a cylinder surface coaxial with the rotation axis 150.

Figure 3:
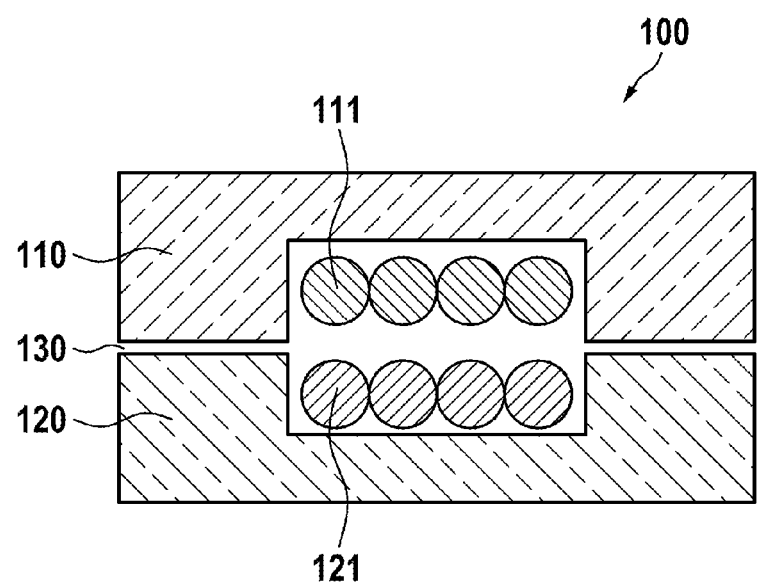
FIG. 3 shows a sectional view of a rotating power transformer.

In FIG. 3, a sectional view of a rotating power transformer is shown.

A primary magnetic core 110 having a primary winding 111 is rotatable against a secondary magnetic core 120 having a secondary magnetic winding 121. Between the primary magnetic core 110 and the secondary magnetic core 120 is an air gap 130.

Figure 4:
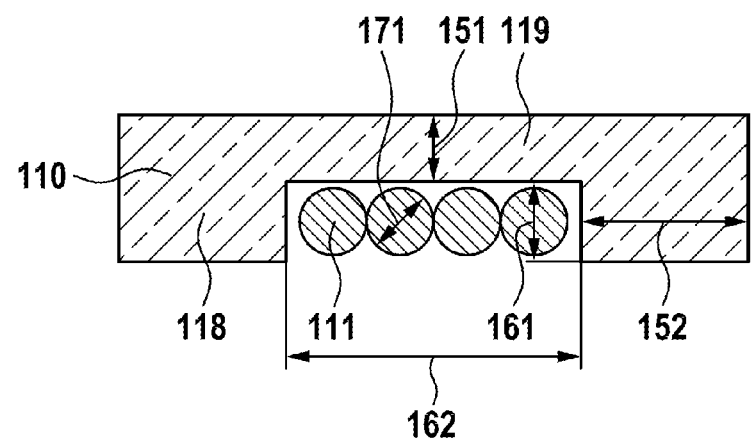
FIG. 4 shows dimensions of a magnetic core.

In FIG. 4, dimensions of a magnetic core are shown. The primary magnetic core 110 has essentially the same dimensions as the secondary magnetic core 120. Therefore, reference is only made to the primary magnetic core 110. It has two legs 118 and a base 119 connecting both legs. The legs 118 have a leg width 152, which is larger than the base height 151. Preferably, the width of each leg 152 is between 1.5- to 5-times the height of the base. Most preferably, the width of each leg 152 is between 2- and 3-times the height of the base. In a most preferred embodiment, the leg width 152 is about 2.5-times the base height 151. The magnetic core has a winding space with a winding space height 161 and a winding space width 162. It is preferred, if the winding space height and the winding space width are adjusted to the diameter 171 of the winding wires forming the individual turns of the winding. In this embodiment, four turns are shown. Accordingly, the winding space width 162 is about 4-times the winding space height 161.

Figure 5:
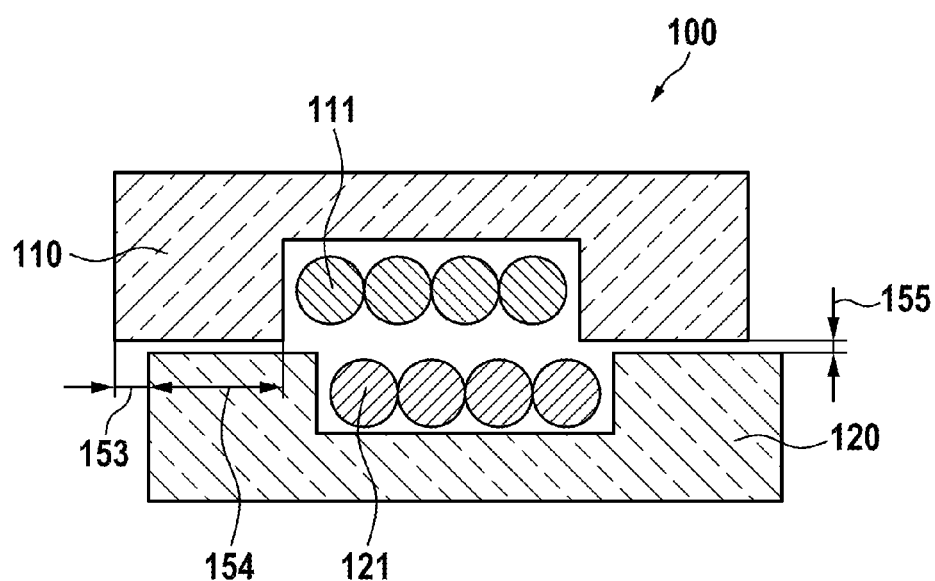
FIG. 5 shows displaced primary and secondary cores.

In FIG. 5, displaced primary and secondary cores are shown. Here, the primary magnetic core 110 is displaced against the secondary magnetic core 120 about a displacement 153 and an air gap width 155. Due to the large leg widths as shown in the previous figure, there remains still a significant overlap between the primary magnetic core 110 and the secondary magnetic core 120 having an overlap length 154, which is still larger than the base height 151. If a regular core as known from prior art would have been used, having a leg width which is the same as the base height, there would be no overlap between the legs of the primary core and the secondary core. Therefore, there would be a very low coupling, which would render the rotating power transformer useless.

Figure 6:
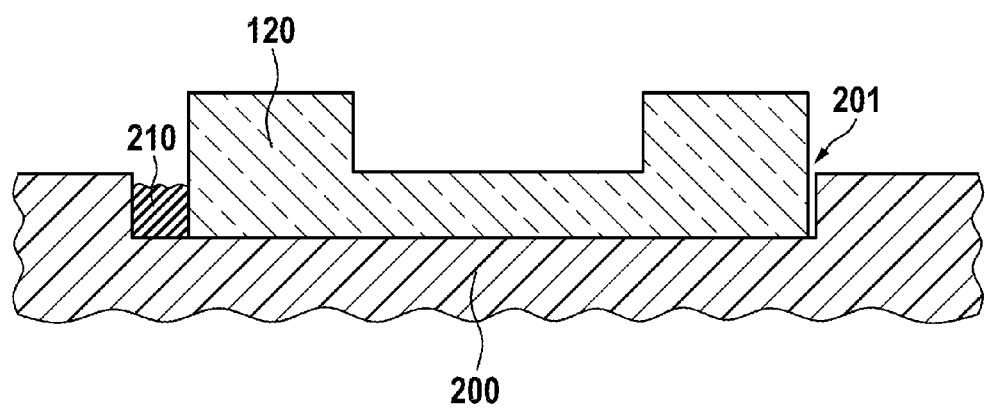
FIG. 6 shows a sectional view of a magnetic core mounted into a base.

In FIG. 6, a sectional view of a magnetic core 120 mounted into a base body 200 is shown. The base body 200 may be a disk- or cylinder-shaped body which preferably has a groove 201 for holding a magnetic core 120. It is preferred, if the groove 201 is wider than the width of the magnetic core 120, resulting in a gap. It is further preferred to have the gap filled with a filler 210 which preferably is an elastic material to compensate for different thermal expansions of the magnetic core and the base.

Figure 7:
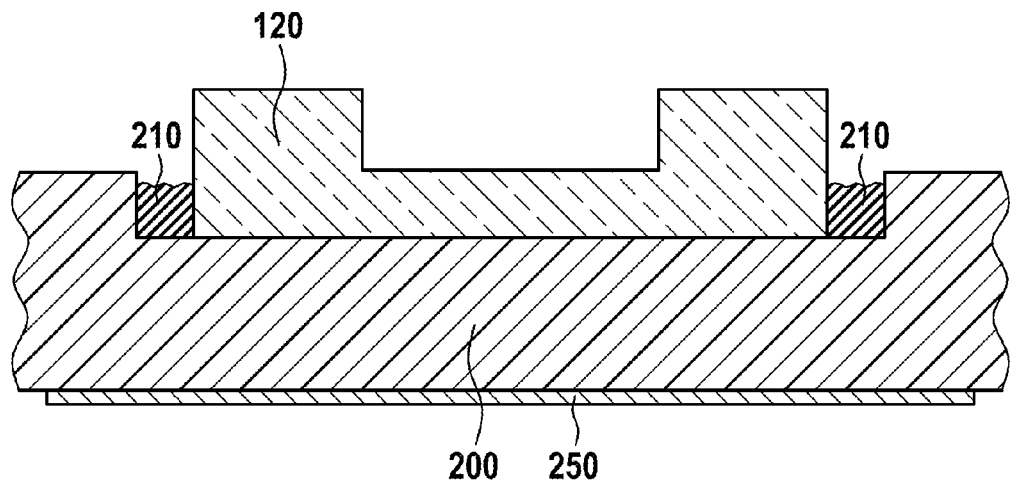
FIG. 7 shows a further sectional view of a magnetic core mounted into a base.

In FIG. 7, a further sectional view of a different embodiment with magnetic core 120 mounted into a base body 200 is shown. Here, there are gaps on both sides of the core, filled with a filler 210. This results in a better distribution of pressure. In this figure, also a shield 250 is provided.

Figure 8:
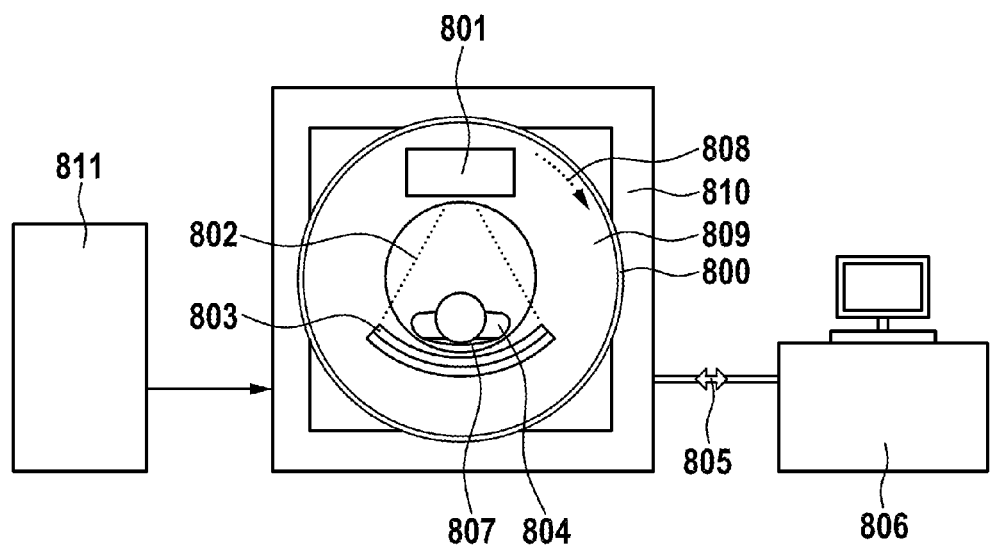
FIG. 8 shows a CT scanner.

FIG. 8 shows schematically a CT (Computed Tomography) scanner gantry. The stationary part is suspended within a massive frame 810. The rotating part 809 of the gantry is rotatably mounted with respect to the stationary part and rotates along the rotation direction 808. The rotating part may be a metal disk which supports an X-ray tube 801, a detector 803 and further electronic and mechanic components. The X-ray tube is for generating an X-ray beam 802 that radiates through a patient 804 lying on a table 807 and which is intercepted by a detector 803 and converted to electrical signals and imaging data thereof. The data obtained by the detector 803 are transmitted via a contactless rotary joint (not shown) to an evaluation unit 806 by means of a data bus or network 805. Electrical power from a stationary power supply unit 811 may be transmitted by an inductive power coupler 800 to the rotating part.

It will be appreciated to those skilled in the art having the benefit of this disclosure that this invention is believed to provide a rotating power transformer. Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

LIST OF REFERENCE NUMERALS 100 rotating power transformer
110 primary magnetic core
111 primary winding
118 leg
119 base
120 secondary magnetic core
121 secondary winding
130 air gap
150 rotation axis
151 base height
152 leg width
153 displacement
154 overlap length
155 air gap width
161 winding space height
162 winding space width
171 wire diameter
200 base body
201 groove
210 filler
250 shield
800 inductive power coupler
801 x-ray tube
802 x-ray beam
803 x-ray detector
804 patient
805 network
806 evaluation unit
807 patient table
808 rotation direction
809 rotating part
810 frame
811 power supply unit 10 Gantry

The invention claimed is:

1. A rotating power transformer comprising
a primary magnetic core having at least one primary winding,
a secondary magnetic core having at least one secondary winding,
wherein the primary magnetic core is in close proximity to the secondary magnetic core and separated therefrom by an air gap,
wherein the primary magnetic core and the secondary magnetic core are rotatable against each other around a rotation axis,
wherein the primary and secondary magnetic cores comprise U-shaped cores with a base connecting two legs, the base having a base height, the two legs having a leg width,
wherein the leg width is more than 1.5-times larger than the base height, and
wherein at least one of the primary magnetic core and the secondary magnetic core comprises at least one of a ferrite material and an iron powder material,
wherein at least one of the primary and secondary magnetic cores is mounted to a base body having a groove with a groove width larger than a width of at least one of the primary and secondary magnetic cores,
and further comprising:
a gap defined by the groove width and the width of the at least one of said primary and secondary magnetic cores, wherein said gap is at least partially filled by a filler,
wherein a material of the at least one of the primary and secondary magnetic cores has a first thermal expansion coefficient, a material of the base body has a second thermal expansion coefficient, a material of the filler has a third thermal expansion coefficient, and
wherein dimensions of said at least one of the primary and secondary magnetic cores, the base body, and the filler are defined such as to have a combination of a thermal expansion of the at least one of the primary and secondary magnetic cores with a thermal expansion of the filler compensate a thermal expansion of the gap in the base body.

2. A rotating power transformer according to claim 1, wherein the primary and secondary magnetic cores have a winding space having a winding space width and a winding space height, said winding space width being N-times said winding space height, where N is a number of turns of a winding wound in one layer.

3. A rotating power transformer according claim 1, wherein the filler includes an elastic material.

4. A rotating power transformer according to claim 1, further comprising a shield either under at least one of the primary and secondary magnetic cores or mounted to a side of the body that is opposite to the groove.

5. A rotating power transformer according to claim 4, wherein the shield comprises a conductive sheet material.

6. A rotating power transformer according to claim 5, wherein the shield comprises a metal sheet.

7. A rotating power transformer according to claim 1, wherein the leg width is between 2- and 3-times the base height.

8. A rotating power transformer according to claim 7, wherein the leg width is 2.5-times the base height.

9. A rotating power transformer comprising
a primary magnetic core having at least one primary winding,
a secondary magnetic core having at least one secondary winding,
wherein the primary magnetic core is in close proximity to the secondary magnetic core and separated therefrom by an air gap,
wherein the primary magnetic core and the secondary magnetic core are rotatable against each other around a rotation axis,
wherein the primary and secondary magnetic cores comprise U-shaped cores with a base connecting two legs, the base having a base height, the two legs having a leg width,
wherein the leg width is between 2- and 3-times the base height, and
wherein at least one of the primary magnetic core and the secondary magnetic core comprises at least one of a ferrite material and an iron powder material.

10. A rotating power transformer according to claim 9, wherein the primary and secondary magnetic cores have a winding space having a winding space width and a winding space height, said winding space width being N-times said winding space height, wherein N is a number of turns of a winding wound in one layer.

11. A rotating power transformer according to claim 9, wherein at least one of the primary and secondary magnetic cores is mounted to a base body having a groove with a groove width larger than a width of at least one of the primary and secondary magnetic cores.

12. A rotating power transformer according to claim 11, further comprising a gap defined by the groove width and the width of the at least one of said primary and secondary magnetic cores, wherein said gap is at least partially filled by a filler.

13. A rotating power transformer according claim 12, wherein the filler includes an elastic material.

14. A rotating power transformer according claim 12, wherein the filler includes a material having a thermal coefficient sufficient to compensate for differences between thermal expansion of the at least one of the primary and secondary magnetic cores and the base.

15. A rotating power transformer according to claim 11, further comprising a shield either under at least one of the primary and secondary magnetic cores or mounted to a side of the body that is opposite to the groove.

16. A rotating power transformer according to claim 15, wherein the shield comprises a conductive sheet material.

17. A rotating power transformer according to claim 9, wherein the leg width is 2.5-times the base height.

* * * * *